United States Patent [19]

Morisaki

[11] Patent Number: 4,973,472
[45] Date of Patent: Nov. 27, 1990

[54] DENTAL PLAQUE INHIBITOR
[75] Inventor: Mayumi Morisaki, Amagasaki, Japan
[73] Assignee: Senju Pharmaceutical Col., Ltd., Osaka, Japan
[21] Appl. No.: 451,745
[22] Filed: Dec. 18, 1989
[30] Foreign Application Priority Data
  Dec. 26, 1988 [JP] Japan .................................. 63-330086
[51] Int. Cl.$^5$ .......................... A61K 7/16; A61K 9/68
[52] U.S. Cl. ........................................ 424/48; 424/49
[58] Field of Search ........................................ 424/48, 49
[56] References Cited

FOREIGN PATENT DOCUMENTS

| | | |
|---|---|---|
| 236120 | 9/1987 | European Pat. Off. . |
| 288969 | 11/1988 | European Pat. Off. . |
| 52-38113 | 9/1977 | Japan . |
| 56-1070 | 1/1981 | Japan . |
| 58-21603 | 5/1983 | Japan . |
| 59-12274 | 3/1984 | Japan . |
| 59-219295 | 12/1984 | Japan . |
| 62-145019 | 6/1987 | Japan . |
| 62-205091 | 9/1987 | Japan . |
| 63-24488 | 5/1988 | Japan . |
| 63-26083 | 5/1988 | Japan . |
| 63-119416 | 5/1988 | Japan . |
| 63-139114 | 6/1988 | Japan . |
| 63-139972 | 6/1988 | Japan . |
| 63-270626 | 11/1988 | Japan . |
| 63-277612 | 11/1988 | Japan . |

OTHER PUBLICATIONS

Yamamoto et al., C.A. 107:242631B (1987).
Yamamoto et al. C.A. 108:38133q (1988).
Tojo et al. C.A. 108:62247t (1988).
Takasu et al. C.A. 110:199208s (1989).
Senoo et al. C.A. 111:45280T (1989).
Ogata et al. C.A. 111:1404872 (1989).

Primary Examiner—Shep K. Rose
Attorney, Agent, or Firm—Wenderoth, Lind & Ponack

[57] ABSTRACT

Provided are dental plaque inhibitor compositions comprising a compound of the formula:

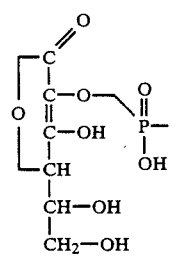

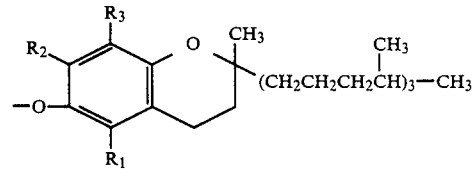

wherein $R_1$, $R_2$ and $R_3$ are the same or different and each is a hydrogen atom or a methyl group or a pharmaceutically acceptable salt thereof.

The compositions inhibit the formation of dental plaque by inhibiting the transformation of sucrose into insoluble polysaccharides.

1 Claim, 1 Drawing Sheet

DENTAL PLAQUE INHIBITOR

BACKGROUND OF THE INVENTION

1. Field of the Invention

The present invention relates generally to the prevention of dental caries, peridontitis, gingivitis and pyorrhoea alveolaris and more particularly to an inhibitor of dental plaque formation which is an etiologic factor in these diseases.

2. Description of Prior Art

Among diseases of the mouth, both dental caries and pyorrhoea alveolaris are major disorders which may lead to a premature loss of teeth and are encountered with high frequency in dental practice. It has by now been well established in the field of dentistry that these diseases are caused by the indiginous bacteria in the oral cavity and, regarding the mechanism of onset, that the presence of a dental plaque is essential. Thus, the sucrose contained in food is transformed into insoluble polysaccharides (hereinafter referred to collectively as insoluble glucan) by glycosyl transferase (hereinafter referred to as GTase), an enzyme extracellularly secreted by *Streptococcus mutans* which is a member of the oral bacterial flora, and as the insoluble glucan is deposited on the surface of the tooth, a dental plaque is formed as a conglomerate of bacterial cells including those of *S. mutans*. Here, the bacterial cells account for about 70 percent of the dental plaque, the figure found by subtracting the combined amount of said insoluble glucan and food residues from the total amount of dental plaque, and as these bacteria metabolize the carbohydrates in food by their glycolytic systems, organic acids such as lactic acid are produced to lower the pH of the dental plaque. When the surface pH of the tooth drops to 5.4 or less, the tooth enamel undergoes decalcification. This is the mechanism of onset and progression of caries. On the other hand, the toxins and other substances elaborated by the bacteria growing in the dental plaque as well as the dead cells irritate the gingiva to cause peridontitis, gingivitis and even pyorrhoea alveolaris.

Since the existence of a dental plaque is, thus, essential to the onset of the two major diseases of the mouth, i.e. carries and pyorrhoea alveolaris, it is believed that these diseases could be effectively prevented if the dental plaque be somehow removed or its formation be forestalled. Along this line of thinking, various approaches have been proposed in recent years. Taking the removal of dental plaque as an example, enzymes for decomposing the insoluble glucan have been disclosed in Japanese Patent Publication No. 38113/1977 (an insoluble glucan-dissolving enzyme derived from a bacterial strain belonging to the genus *Flavobacterium*), Japanese Patent Publication No. 1070/1981 (an insoluble glucan-decomposing enzyme derived from a strain of the genus *Pseudomonas*) and Japanese Patent Publication No. 12274/1984 (an α-1,3-glycosidic bond-cleaving enzyme derived from a strain belonging to the genus *Streptomyces*), for instance. An enzyme system discharging the dual function of removing dental plaques and destroying bacteria has been disclosed in Japanese Patent Publication No. 21603/1983 (a combination of dextranase with a bacterial cell wall-lysing enzyme). For the prevention of dental plaque formation, several substances showing specific antibacterial activity against *S. mutans* have been disclosed in Japanese laid-open Patent Application KOKAI No. 63-119416/1988 (gymnemic acids) and Japanese Patent Publication No. 26083/1988 (triterpene compounds). On the other hand, as suggested in Japanese Patent Publication No. 24488/1988 and Japanese laid-open Patent Application KOKAI 63-277612/1988, attempts have been made to block the process of formation of a dental plaque, i.e. agglomeration of oral bacteria to form a bacterial mass, by inhibiting the very production of insoluble glucan by *S. mutans*.

Despite the above assiduous research toward removal or prevention of a dental plaque, there is no universally accepted dental plaque remover or inhibitor that is fully effective and fully satisfactory, and there has been a standing demand for the development of a powerful dental plaque remover or inhibitor substance.

Inspired by the thought that if the GTase of *Streptococcus mutans* could be directly inhibited in the stage of its transformation of sucrose to insoluble glucan, the production of insoluble glucan would be effectively prevented to suppress formation of a dental plaque with very high efficiency, the inventor of the present invention isolated and partially purified said enzyme from cultures of *S. mutans* and using the crude enzyme, screened a large number of substances in respect of GTase inhibitory activity, as well as the intensity of such activity. Surprisingly, the inventor discovered that several compounds of the following general formula (I)

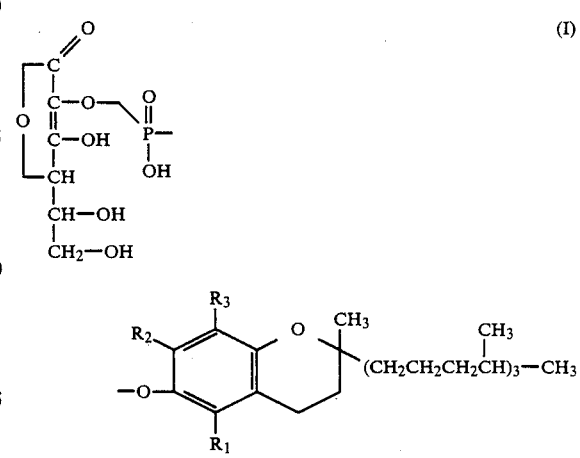

wherein $R_1$, $R_2$ and $R_3$ may be the same or different and each represents a hydrogen atom or a methyl group or a pharmaceutically acceptable salt thereof have potent GTase-inhibitory activity and that they completely inhibit the adhesion of *Streptococcus mutans* to the surface of an human tooth in a culture system favorable to the production of said insoluble glucan. The present invention has been accomplished on the basis of the above findings.

SUMMARY OF THE INVENTION

The present invention is, therefore, directed to a dental plaque inhibitor composition comprising a compound of formula (I) or a pharmaceutically acceptable salt thereof.

The compound of formula (I) which is used as the principal active ingredient of the dental plaque inhibitor composition of the invention can be easily synthesized by linking the corresponding compound of formula (II)

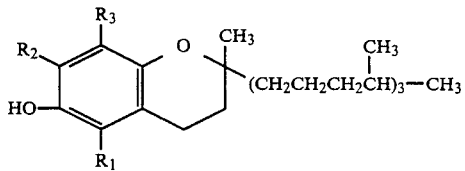

(II)

wherein the symbols have the same meanings as defined above, to ascorbic acid through phosphoric acid in the manner of esterification, that is to say by a method analogous to the method described in European Patent Publication No. 0,236,120 A2.

Referring to the pharmaceutically acceptable salt of the compound of formula (I), there may be mentioned the corresponding salts with alkali metals such as sodium, potassium, etc., and salts with alkaline earth metals such as calcium, magnesium and so on. Any of these salts can be employed with advantage.

DETAILED DESCRIPTION OF THE INVENTION

Figure 1:
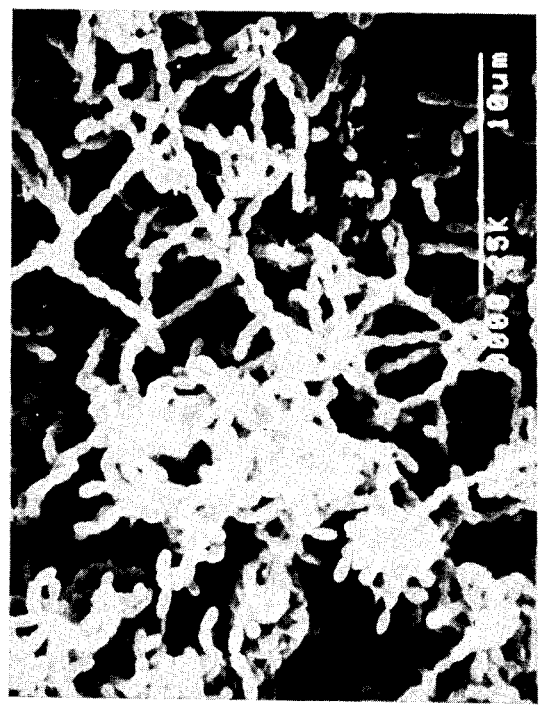
FIG. 1 is a scanning electron micrograph (x 4,000) in lieu of a drawing which shows the morphology of microorganisms grown on the surface of the tooth cultured in the absence of Substance 1.

It should also be understood that the dental plaque inhibitor composition of the present invention may contain, in addition to said compound of formula (I) or pharmaceutically acceptable salt thereof, such additives as abrasives or polishing agents (e.g. dibasic calcium phosphate, calcium carbonate, calcium pyrophosphate, insoluble sodium metaphosphate, amorphous silica, crystalline silica, aluminosilicate, aluminum oxide, aluminum hydroxide, resins, etc.), binders (e.g. polyvinyl alcohol, carboxymethylcellulose, hydroxyethylcellulose, gum arabic, alginates, carrageenan, etc.), viscosity builders (e.g. glycerol, polyethylene glycol, propylene glycol, etc.), surfactants (e.g. Polysorbate 80, sodium laurylsulfate, sodium dodecylbenzenesulfonate, sodium oleate, sodium stearate, polyoxyethylene sorbitan monolaurate, sucrose fatty acid ester, N-acylglutamic acids, sodium N-lauroyl sarcosinate, etc.), sweeteners (e.g. glucose, maltose, sorbitol, saccharin sodium, stevioside, neohesperidyldihydrochalcone, glycyrrhizin, perillartine, p-methoxycinnamaldehyde, etc.), tooth decay inhibitors (e.g. sodium fluoride, sodium monofluoroacetate, stannous fluoride, etc.), flavors or corrigents (e.g. menthol, eugenol, thymol, eucalyptol, methyl salicylate, etc.), ointment bases (e.g. white petrolatum, liquid paraffin, Plastibase, stearyl alcohol, etc.), preservatives (e.g. chlorhexidine digluconate, cetylpyrridinium chloride, paraben, etc.), gum base, colors, ethanol and so on in appropriate proportions. The resulting composition may take various dosage or application forms such as toothpastes, toothpowders, liquid dentifrices, tablets, mouth rinses, gargles, troches, chewing gums, buccal ointments and so on. These dosage forms can be manufactured by the established procedures, and said compound of formula (I) or pharmaceutical salt thereof may be added in any stage of manufacture. The level of addition is preferably 0.05 w/v % to 5.0 w/v % and for still better results, 0.1 w/v % to 2.0 w/v %, based on the total product. In the case of liquid dentifrices, mouth rinses or gargles, the pH of the liquids is preferably adjusted to the range of 4.0 to 9.0.

Among said compounds of formula (I) and pharmaceutically acceptable salts to be used as active ingredients of the present invention, the compounds disclosed in Japanese laid-open Patent Application KOKAI No. 59-219295/1984 referred to above and the compounds disclosed in Japanese laid-open Patent Applications No. 62-145019/1987, No. 62-205091/1987, No. 63-139114/1988, No. 63-139972/1988 and No. 63-270626/1988, all of which can be synthesized in substantially the same manner as described in said Japanese laid-open Patent Application No. 59-219295/1984, are known to have antioxidant activity, anti-inflammatory activity, antiulcer activity, antidandruff activity, cataract preventive activity, menopausal syndrome preventive and therapeutic activity and/or cosmetic activity. It is quite surprising that the compounds of formula (I) and pharmaceutically acceptable salts thereof to be employed in the present invention have dental plaque formation-inhibitory activity which is quite alien to the above-mentioned known activities.

Thus, the present invention prevents the production of insoluble glucan by acting directly on GTase which is the extracellular bacterial enzyme involved in the transformation of sugar into insoluble glucan, so that the formation of a dental plaque as an integral mass of bacterial cells entangled by insoluble glucan is successfully prevented. As a consequence, the decalcification of the enamel by lactic and other acids, which are produced as metabolic products of glycolysis in the bacteria on the surface of the tooth, and the disorder of the gingiva due to irritation by dead bacterial cells and toxins are successfully precluded. Thus, the formation of caries and the onset of peridontitis, gingivitis and pyorrhea alveolaris can be effectively prevented by the invention.

Experiments

Experiment 1 GTase-inhibitory activity

The enzyme GTase was prepared from *Streptococcus mutans* and using sucrose as the substrate, the inhibitory effect of the test substances on the formation of insoluble glucan was determined.

Method

Preparation of crude GTase

The preparation of GTase was carried out in accordance with the description in Methods for Isolation of Microorganisms (Kazue Yamazato (ed.): R&D Planning), page 733, (1) Preparation of cell-free GTase. Thus, *Streptococcus mutans* ATCC 33402 was cultured (inoculum size 1%) in brain heart infusion broth (Difco; hereinafter referred to as BHI medium) under stationary conditions at 37° C. for 18 hours and the resulting culture was centrifuged at 4,000 rpm for 10 minutes. The supernatant was taken and ammonium sulfate was added at a final concentration of 60% saturation. The mixture was gently stirred at 4° C. overnight for salting-out and the precipitate was dissolved in 5 mM potassium phosphate buffer (pH 6.5). This solution was then dialyzed against the same buffer at 4° C. overnight to give a crude GTase preparation.

Assay of GTase activity

The assay of GTase activity was carried out by the method described in Methods for Isolation of Microorganisms (ibid), page 733, (2) Assay of activities in microbial culture filtrates with minor modification. Thus, the solution prepared as per Tables 1 and 2 was used as a test solution and the corresponding solution prepared by using the same quantity of distilled water in lieu of the test substance solution in otherwise the same composition was used as a control solution. Test tubes were filled with 5 ml aliquots of the test solution or the control solution and allowed to stand in upright position at 37° C. for 16 hours. After completion of the reaction each tube was shaken well to agitate the reaction system and the optical density at 550 nm was measured to find the degree of turbidity. The inhibitory activity of the test substance against GTase was calculated as a percentage with the turbidity of the control reaction system being taken as 100%.

TABLE 1

| Composition of substrate-test substance solution | |
|---|---|
| Sucrose | 1.0% |
| Sodium azide | 0.02% |
| Test substance | 0.01-1.0% |
| 50 mM Potassium phosphate buffer (pH 6.5) q.s. | |
| Total | 100 ml |

TABLE 2

| Composition of reaction system | |
|---|---|
| Substrate-test substance solution | 5000 μl |
| GTase | 100 μl |
| Total | 5100 μl |

Preparation of test substance solutions

Among the substances falling under the purview of the present invention, those mentioned in Table 3 (Substances 1 through 6) were used as test substances.

TABLE 3

| Substance | $R_1$ | $R_2$ | $R_3$ |
|---|---|---|---|
| Substance 1 | Methyl | Methyl | Methyl |
| 2 | Methyl | H | Methyl |
| 3 | H | Methyl | Methyl |
| 4 | H | H | Methyl |
| 5 | H | H | H |
| 6 | Methyl | Methyl | Methyl |

(Note)
Substances 1-5: potassium salts,
substance 6: sodium salt)

Experiment 1—1 Inhibitory activity of test substances

For each of the substances mentioned in Table 3, the GTase activity at the test substance concentration of 0.5% in the reaction system was assayed to estimate the inhibitory activity of the test substance.

Experiment 1-2 Correlation between test substance concentration and inhibitory activity For Substance 1, GTase activity was assayed in the reaction system corresponding to each concentration of the test substance in the range of 0.01% to 1.0% and to obtain correlation between inhibitory activity and test substance concentration.

Experiment 1-3 Correlation between reaction system pH and inhibitory activity For Substance 1 at a concentration of 0.5%, either aqueous sodium hydroxide solution or hydrochloric acid was added to portions of the substrate-test substance solution shown in Table 1 to prepare solutions adjusted to pH 4, 5, 6, 7 and 8, respectively, and using each of these solutions, the reaction was carried out at the corresponding pH. The GTase activity at each pH was assayed and the correlation between reaction system pH and inhibitory activity was studied.

Results

1—1 Inhibitory activity of each test substance

All of the under-mentioned test substances almost completely inhibited the formation of insoluble glucan at the concentration of 0.5%. The rate of GTase inhibition was invariably in excess of 90%.

TABLE 4

| Test substance | Optical density of reaction system | % Inhibition |
|---|---|---|
| Control | 0.55 | — |
| Substance 1 | 0.04 | 92.7 |
| 2 | 0.03 | 94.5 |
| 3 | 0.03 | 94.5 |
| 4 | 0.03 | 94.5 |
| 5 | 0.03 | 94.5 |
| 6 | 0.02 | 95.8 |

Experiment 1-2 Correlation between test substance concentration and inhibitory activity In the concentration range of 0.01% to 1.0%, Substance 1 inhibited the formation of insoluble glucan as indicated below in the Table. The inhibitory activity of Substance 1 was concentration-dependent and the inhibition rates were not less than about 90% at 0.075% and higher concentrations and about 60% even at the concentration of 0.01%.

TABLE 5

| Concentration (%) | Optical density of reaction system | % Inhibition |
|---|---|---|
| Control | 0.496 | — |
| 1.0 | 0.02 | 96.0 |
| 1.0 | 0.02 | 96.0 |
| 0.5 | 0.02 | 96.0 |
| 0.25 | 0.02 | 96.0 |
| 0.1 | 0.02 | 96.0 |
| 0.075 | 0.05 | 89.9 |
| 0.05 | 0.20 | 59.7 |
| 0.025 | 0.20 | 59.7 |
| 0.01 | 0.20 | 59.7 |

Experiment 1-3 Correlation between reaction system pH and inhibitory activity As shown below, Substance 1 at a concentration of 0.5% inhibited the formation of insoluble glucan over the pH range of 4 through 8. The inhibition rate was not less than 90% at pH 6 and 7 where GTase showed the peak activity and was about 70% at pH 5 where the very GTase activity showed some decrease in the control system. At pH 4 or 8, the GTase activity was negligible even in the control system, thus rendering it meaningless to calculate the inhibition rate. In the pH range where GTase was active, the formation of insoluble glucan was invariably very slight in the reaction systems containing Substance 1 at a contraction of 0.5%.

TABLE 6

| pH | Optical density Control | Test substance | % Inhibition |
| --- | --- | --- | --- |
| 4 | 0.08 | 0.05 | — |
| 5 | 0.35 | 0.06 | 71.4 |
| 6 | 0.62 | 0.05 | 91.9 |
| 7 | 0.59 | 0.03 | 94.9 |
| 8 | 0.05 | 0.02 | — |

Experiment 2 Prevention of the adhesion of tooth decaying bacteria to the human tooth Method Two test tubes were respectively filled with BHI medium containing 5% of sucrose and a sterilized human tooth was suspended in each of the tubes using a stainless steel wire. After Substance 1 was added to one of the tubes at a final concentration of 0.5%, a culture of *Streptococcus mutans* ATCC 330402 grown in BHI medium at 37° C. for 18 hours was added to both tubes at a final concentration of $10^8$ CFU/ml. The tubes were further incubated at 37° C. for 6 hours, at the end of which time the teeth were taken out, rinsed and observed with a scanning electron microscope at a magnification of x 4,000.

Results

Figure 2:
FIG. 2 is a scanning electron micrograph (x 4,000) in lieu of a drawing which shows the morphology of microorganisms grown on the surface of the tooth cultured in the presence of Substance 1.

FIG. 1 is a scanning electron micrograph (x 4,000) showing the surface condition of the tooth incubated in the absence of Substance 1 and FIG. 2 is a similar scanning electron micrograph (x 4,000) showing the surface condition of the tooth incubated in the presence of Substance 1. As apparent from FIG. 1, the tooth cultured without addition of Substance 1 showed many adherent cells and colonies of *Streptococcus mutans* on the surface. In contrast, the tooth cultured in the presence of Substance 1 showed neither adherent bacterial cells nor colonies on the surface as apparent from FIG. 2, demonstrating clearly that adhesion of bacterial cells and subsequent formation of colonies on the tooth surface are completely inhibited by Substance 1.

The following examples are further illustrative of the dental plaque inhibitor composition of the present invention.

Example 1 Toothpaste

According to the formula below, glycerol, hydroxyethyl-cellulose, saccharine sodium, propylparaben, substance 1 and flavor are added to water and mixed well. After hydration of hydroxyethylcellulose is attained, dibasic calcium phophate and sodium laurylsulfate are added to the mixture and mixed well to make paste.

| Ingredient | Weight (%) |
| --- | --- |
| Dibasic calcium phosphate | 50.0 |
| Sodium laurylsulfate | 2.0 |
| Glycerol | 20.0 |
| Hydroxyethylcellulose | 1.0 |
| Substance 1 | 2.0 |
| Saccharin sodium | 0.1 |
| Flavor | 1.0 |
| Propylparabe | 0.005 |
| Water | q.s. |

-continued

| Ingredient | Weight (%) |
| --- | --- |
| Total | 100 |

Example 2 Toothpowder

According to the following formulation, the ingredients are mixed well to make fine powder.

| Ingredient | Weight (%) |
| --- | --- |
| Calcium carbonate | 75.0 |
| Glycerin | 10.0 |
| Flavor | 1.0 |
| Propylparaben | 0.005 |
| Sodium laurylsulfate | 1.3 |
| Substance 2 | 1.0 |
| Saccharin sodium | 0.1 |
| Water | q.s. |
| Total | 100 |

Example 3 Liquid dentifrice

According to the following formula, the ingredients are mixed well to dissolve. PH of the solution are then adjusted to about 5.0 with dilute hydrochloric acid or sodium hydroxide solution, and the solution is subjected to filtration.

| Ingredient | Weight (%) |
| --- | --- |
| Glycerin | 30.0 |
| Ethanol | 5.0 |
| Sodium polyacrylate | 5.0 |
| Substance 3 | 2.0 |
| Sodium laurylsulfate | 2.0 |
| Saccharin sodium | 0.1 |
| Flavor | 1.0 |
| Water | q.s |
| Total | 100 |

Example 4 Mouth wash

According to the following formula, the ingredients are mixed to dissolve. PH of the solution is adjusted to about 6.5 with addition of 1N hydrochloric acid or 1N sodium hydroxide solution.

| Ingredient | Weight (%) |
| --- | --- |
| Ethanol (95%) | 5.0 |
| Propylene glycol | 20.0 |
| Sorbitol | 0.5 |
| Menthol oil | 0.1 |
| Substance 4 | 0.1 |
| Water | q.s. |
| Total | 100 |

Example 5 Tablets for gargling

According to the following formula, tablets are prepared by conventional method.

| Ingredient | Weight (%) |
| --- | --- |
| Sodium bicarbonate | 53.0 |
| Citric acid | 16.0 |
| Sodium dihydrogen phosphate | 16.0 |
| Polyethylene glycol 4000 | 5.0 |
| Flavor | 5.0 |

9
-continued

| Ingredient | Weight (%) |
| --- | --- |
| Substance 5 | 5.0 |
| Total | 100 |

Example 6 Liquid gargles

According to the following formula, the ingredients are mixed well to dissolve. PH of the solution are then adjusted to about 5.0 with 1N hydrochloric acid or 1N sodium hydroxide solution, and the solution is subjected to filtration.

| Ingredient | Weight (%) |
| --- | --- |
| Substance 1 | 0.2 |
| Boric acid | 5.0 |
| Borax | 0.5 |
| Water | q.s. |
| Total | 100 |

Example 7 Troche

According to the following formula, troches are prepared by conventional method.

| Ingredient | Weight (%) |
| --- | --- |
| Gum Arabic | 8.0 |
| Glucose | 78.0 |
| Substance 1 | 2.0 |
| Flavor | 1.0 |
| Water | q.s. |
| Total | 100 |

Example 8 Chewing gum

According to the following formula, chewing gum is prepared by conventional method.

| Ingredient | Weight (%) |
| --- | --- |
| Gum base | 30.0 |
| Xylitol | 35.0 |
| Sorbitol | 30.9 |
| Substance 1 | 0.1 |
| Flavor | 1.0 |
| Calcium carbonate | 3.0 |
| Total | 100 |

10
Example 9 Buccal ointment

According to the formula below, buccal ointment is prepared by conventional method.

| Ingredient | Weight (%) |
| --- | --- |
| Substance 1 | 0.5 |
| Plastibase | 40.0 |
| White petrolatum | 5.0 |
| Liquid paraffin | 20.0 |
| Carboxymethylcellulose | 34.5 |
| Total | 100 |

What is claimed is:

1. A method for preventing dental plaque formation in a mammal having, as a member of the oral bacterial flora, *Streptomyces mutans* which extracellularly secretes glycosyl transferase which transforms sugar into insoluble glucan which entangles and adheres bacteria on tooth surfaces, forming dental plaque, which comprises bringing into contact with the tooth surfaces in the oral cavity of the mammal an effective amount of a compound of the formula (I):

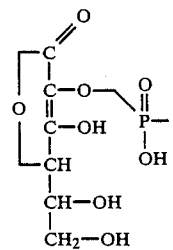

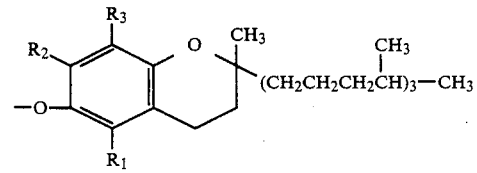

wherein $R_1$, $R_2$ and $R_3$ are the same or different and each is a hydrogen atoms or a methyl group, or a pharmaceutically acceptable salt thereof, in the form of toothpaste, toothpowder, liquid dentifrice, mouth wash, liquid gargles, troche, chewing gum or buccal ointment.

* * * * *